United States Patent [19]

Kobayashi

[11] Patent Number: 4,834,527
[45] Date of Patent: May 30, 1989

[54] WORKING DISTANCE ALIGNMENT OPTICAL SYSTEM FOR OPHTHALMOLOGICAL INSTRUMENT

[75] Inventor: Katsuhiko Kobayashi, Tokyo, Japan

[73] Assignee: Tokyo Kogaku Kikai Kabushiki Kaisha, Tokyo, Japan

[21] Appl. No.: 99,605

[22] Filed: Sep. 22, 1987

[30] Foreign Application Priority Data

Sep. 24, 1986 [JP] Japan ................................. 61-225325

[51] Int. Cl.$^4$ .............................................. A61B 3/14
[52] U.S. Cl. .................................................. 351/208
[58] Field of Search ....................... 351/206, 207, 208; 128/648, 652

[56] References Cited

U.S. PATENT DOCUMENTS

4,180,323 12/1979 Persson et al. ................. 351/208 X

Primary Examiner—Rodney B. Bovernick
Attorney, Agent, or Firm—Finnegan, Henderson, Farabow, Garrett & Dunner

[57] ABSTRACT

A working distance alignment optical system for use in an ophthalmological instrument includes a target projecting optical system for projecting a target to a cornea of an eye to be tested, and a target image observing optical system for observing an image of the target in the cornea from the diagonal direction with respect to the target projecting optical system. The working distance alignment optical system is characterized in that at least one of the target projecting optical system and the target image observing optical system is provided with an optical element whose optical working surface is a toric surface.

11 Claims, 8 Drawing Sheets

(IN WDo = WD)

FIG. 4

(IN WDo > WD)

FIG. 5

(IN WDo < WD)

(IN WDo > WD)

FIG. 12 PRIOR ART (IN WDo = WD)

FIG. 13 PRIOR ART (IN WDo < WD)

FIG. 14
PRIOR ART

WORKING DISTANCE ALIGNMENT OPTICAL SYSTEM FOR OPHTHALMOLOGICAL INSTRUMENT

BACKGROUND OF THE INVENTION

1. Field of the Invention

This invention relates to an improvement of a working distance alignment optical system for use in an ophthalmological instrument such as refractometer, retina camera, ophthalmometer, noncontact type tonometer, etc.

2. Related Art of the Invention

A conventional ophthalomological instrument such as refractometer, retina camera, ophthalmometer, noncontact type tonometer, etc, includes a working distance alignment optical system for properly setting a working distance of an apparatus main body with respect to an eye to be tested.

Figure 10:
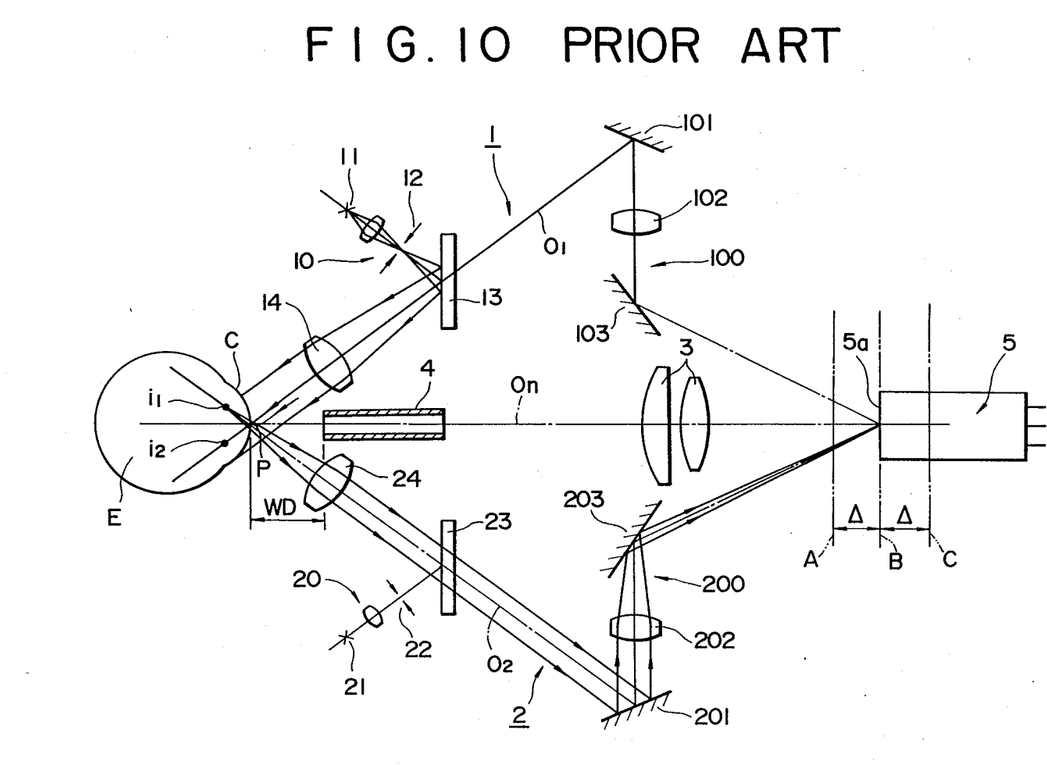
FIG. 10 is a schematic view of a conventional working distance alignment optical system for use in an ophthalmological instrument.

FIG. 10 illustrates one example of such a conventional working distance alignment optical system as mentioned above. The working distance alignment optical system of FIG. 10 is included in a noncontact type tonometer. This working distance alignment optical system is used for properly setting a working distance WD of an air pulse discharging nozzle 4 of a noncontact type tonometer with respect to an eye to be tested or objective eye E.

In FIG. 10, reference numeral 1 denotes a first optical system, and 2 denotes a second optical system. The first and second optical systems 1 and 2 are symmetrically disposed with an axis On as a medium. The first optical system 1 includes a first target image projecting optical system 10, and a first target image observing optical system 100. The optical axis $O_1$ of the first target image observing optical system 100 is partly common with the optical axis of the first target image projecting optical system. The second optical system 2 includes a second target image projecting optical system 20 and a second target image observing optical system 200. The optical axis $O_2$ of the second target image observing optical system 200 is partly common with the optical axis of the second target image projecting optical system 20.

The first target image projecting optical system 10 includes a light source 11 and an aperture 12. The aperture 12 is disposed in front of the light source 11. The first target image observing optical system 100 includes a half mirror 13 and a projecting lens 14 in the midway of the optical axis $O_1$. A ray of the light source 11 passes the aperture 12 and is reflected by a half mirror 13 towards the projecting lens 14. The projecting lens 14 has a focus at the position of the aperture 12. The ray of the light source 11 is converted into a parallel pencil of rays by the projecting lens 14. The projecting lens 14 projects the parallel pencil of rays as a target ray towards the cornea C of the objective eye E. The target ray becomes a reflecting ray for forming a virtual image $i_1$ by specular reflection of the cornea C.

The second target image observing optical system 200 includes a half mirror 23, and a projecting lens 24 in the midway of the optical axis $O_2$. The reflecting ray for forming the virtual image $i_1$ passes the projecting lens 24 and then passes the half mirror 23. The reflecting ray which has passed the half mirror 23, proceeds towards an imaging lens 202 between the mirrors 201 and 203 of the second target image observing optical system 200. The reflecting ray, which forms the virtual image $i_1$ is formed as a target image $i_1'$ by the imaging lens 202 on a photosensitive surface 5a of an image pickup tube 5. This target image $i_1'$ is displayed on a monitor TV (not shown) for observation.

Similarly, the second target image projecting optical system 20 of the second optical system 2 includes a light source 21 and an aperture 22. The aperture 22 is disposed in front of the light source 21. The ray of the light source 21 passes the aperture 22 and reflected by a half mirror 23 towards the projecting lens 24. The projecting lens 24 has a focus at the position of the aperture 22. The ray of the light source 21 becomes a parallel pencil of rays by the projecting lens 24. The projecting lens 24 projects the parallel pencil of rays towards the cornea C of the objective eye E as a target ray. The target ray becomes a reflecting ray for forming a virtual image $i_2$ by specular reflection of the cornea C. The reflecting ray for forming the virtual image $i_2$ passes the projecting lens 14 and then passes the half mirror 13. After passing the half mirror 13, the reflecting ray proceeds towards an imaging lens 102 between mirrors 101 and 103 of the first target image observing optical system 100. The reflecting ray for forming the virtual image $i_2$ is formed as a target image $i_2'$ by the imaging lens 102 on the photosensitive surface 5a of the image pickup tube 5.

As is shown in FIG. 10, when an intersecting point of the optical axes $O_1$ and $O_2$ of the first and second optical systems 1 and 2 and the axis On of the air pulse discharging nozzle 4 is brought to be in alignment with the corneal vertex, the virtual images $i_1$ and $i_2$ are situated on the focussing plane of the cornea C and on the optical axes $O_1$ and $O_2$. At that time, a normal working distance $WD_o$ is obtained when the target images $i_1'$ and $i_2'$ are overlapped with each other on the photosensitive surface 5a of the image pickup tube 5. Since the conventional working distance alignment optical system aligns the working distance using the first and second optical systems 1 and 2, it has the advantage in that the working distance can be more accurately aligned compared with one which depends only on sharpness of a target image.

The conventional working distance alignment optical system of FIG. 10 includes an objective lens 3. This objective lens 3 has such a function as to image an anterior portion image of the objective eye E on the photosensitive surface 5a. Therefore, the user of this ophthalmological instrument can observe the anterior portion image at the same time when he observes the target images $i_1'$ and $i_2'$. The above-description is disposed in the specification of a patent application which the present applicant filed in the United State of America under Ser. No. 801,960 on Nov. 26, 1985 now U.S. Pat. No. 4,665,723.

However, since the conventional working distance alignment optical system has target image observing optical systems 100 and 200, the optical axes $O_1$ and $O_2$ (optical axes of the target image projecting optical systems 10 and 20) are diagonally intersected at one point on the axis On (in other words, the target image observing optical systems observe target images in the cornea from the diagonal direction with respect to the target image projecting optical systems), even if the cornea C is a spherical reflecting surface, when the target image observing optical systems 100 and 200 (or target image projecting optical systems 10 and 20) are discussed, the radius of curvature is different in the sagittal image surface and the meridional image surface. Accordingly, the first and second optical systems 1 and 2 work in such a manner as to produce an astigmatism.

Figure 11:
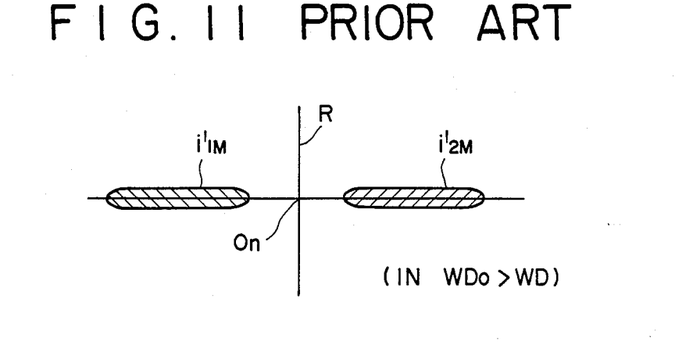
FIGS. 11 through 13 illustrate imaging states of a target image obtained by the conventional working distance alignment optical system for use in an ophthalmological instrument.
Figure 13:
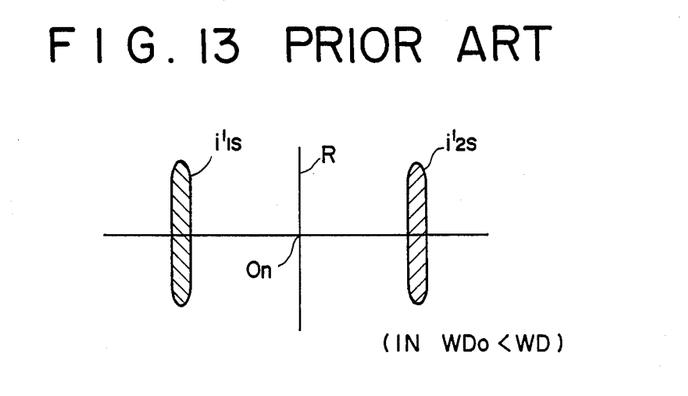

For example, when the working distance WD is smaller than a normal working distance $WD_o$, the photosensitive surface 5a is in a position shown by two-dot chain line A of FIG. 10. At that time, the target images $i_1'$ and $i_2'$ formed on the photosensitive surface 5a becomes, for example, an ellipse with a longitudinal axis in the lateral direction and having a large eccentricity as shown in FIG. 11. On the other hand, when the working distance WD is larger than the normal working distance $WD_o$, the photosensitive surface 5a is in a position shown by two-dot chain line C of FIG. 10. At that time, the target images $i_1'$ and $i_2'$ formed on the photosensitive surface 5a become an ellipse with a longitudinal axis in the vertical direction and having a large eccentricity as shown in FIG. 13. This fact also will be understood from an analysis of an MTF (modulation transfer function) graph of FIG. 14 and the illustration of an optical path.

Figure 12:
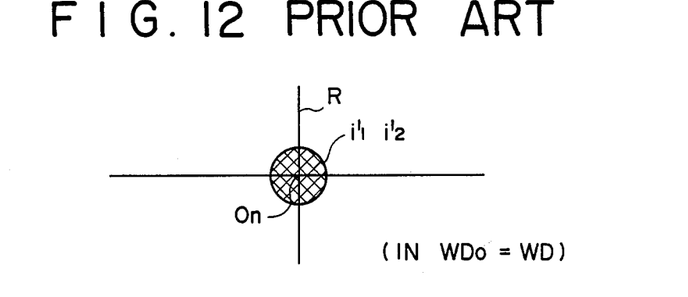

Namely, the target images $i_1'$ and $i_2'$ respectively become sharp images on the meridional image surface M and the sagittal image surface S. However, in the case the working distance WD is equal to the normal working distance $WD_o$, the photosensitive surface 5a is in a position shown by two-dot chain line B of FIGS. 10 and 14. At that time, MTF of the target images $i_1'$ and $i_2'$ is extremely small as apparent from FIG. 14. Accordingly, when the photosensitive surface 5a is in the position shown by the two-dot chain line B, a circle of least confusion CLC becomes large and only vague target images $i_1'$ and $i_2'$ can be obtained as shown in FIG. 12.

Figure 14:
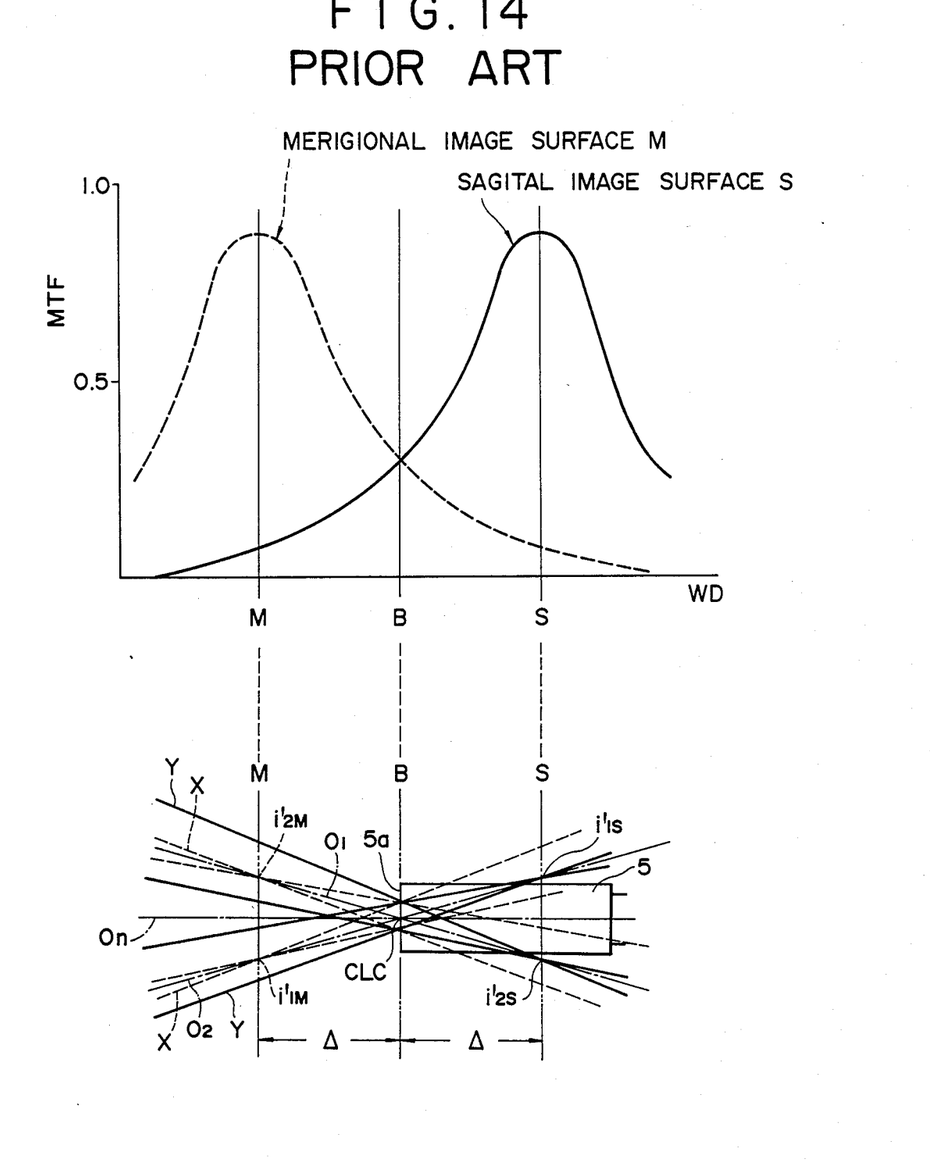
FIG. 14 is an illustration for showing a relation between an MTF graph of the conventional working distance alignment optical system and an optical path for a ray reaching a photosensitive surface.

In FIG. 14, reference symbolic characters $i_{1M}'$ and $i_{2M}'$ denote target images in a position on the meridional image surface M, whereas reference symbolic characters $i_{2S}'$ and $i_{2S}'$ denote target images in a position on the sagittal image surface S. In FIG. 14, a broken line X denotes a meridional image ray and another broken line Y denotes a sagittal ray.

Therefore, although the conventional working distance alignment optical system has the advantage in that the working distance is more accurately aligned compared with one which depends only on sharpness of a target image, since the working distance is aligned based on coincidence or noncoincidence of the target images $i_1'$ and $i_2'$ having a large diffusing amount, the accuracy thereof is naturally limited, no more accuracy can be expected in alignment of the working distance.

Furthermore, it an ophthalmological instrument, it is a general practice that the working distance is aligned and in addition, an alignment is performed in the vertical and horizontal directions within a plane perpendicular to the optical axis (axis On). To this end, the observing optical system is provided with a reticle comprising a cross line R. The intersecting point of the cross line R is located, for example, on the axis On of the air pulse discharging nozzle. The vertical and horizontal alignment are performed by the intersecting point of the cross line R and the target images $i_1'$ and $i_2'$. However, when the diffusion amount of the target images $i_1'$ and $i_27$ is large, the vertical and horizontal alignment accuracy is also decreased.

Furthermore, in the case the circle of least confusion CLC is large, the target images $i_1'$ and $i_2'$ are always diffused in a circular shape which makes it difficult to judge whether the ophthalmological instrument main body should be moved forward or backward during the alignment of the working distance.

SUMMARY OF THE INVENTION

It is therefore an object of the present invention to provide a working distance alignment optical system in which more alignment accuracy of the working distance can be expected, it an ophthalmological instrument including a working distance alignment optical system of the type in which a target image observing optical system diagonally intersects with respect to a target image projecting optical system.

A second object of the present invention is to provide a working distance alignment optical system, in which it can be easily judged whether the apparatus main body including the working distance alignment optical system should be approached to the objective eye or brought away from the objective eye during the alignment of the working distance.

The above-mentioned first object can be attained by proving an optical element whose optical working surface is a toric surface, to at least one of a target image projecting optical system for projecting a target image to the cornea of the objective eye and a target image observing optical system for observing the target image in the cornea from the diagonal direction with respect to the target image projecting optical system.

The above-mentioned second object of the present invention can be attained by forming the toric surface as such that the astigmatism of the target image observing optical system will be remained by a desired amount.

DETAILED DESCRIPTION OF THE EMBODIMENTS

First Embodiment

Figure 1:
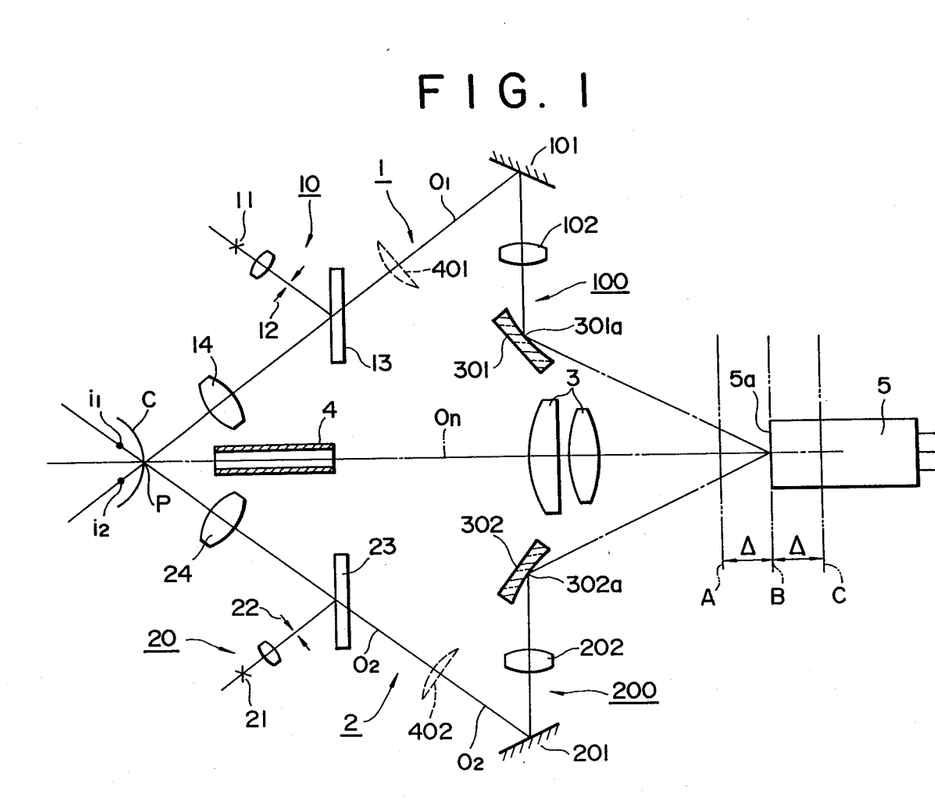
FIG. 1 is a schematic view showing a first embodiment of a working distance alignment optical system for use in an ophthalmological instrument according to the present invention.

FIG. 1 illustrates a first embodiment of an alignment optical system for use in an ophthalmological instrument according to the present invention. Since the structure of the alignment optical system for use in an ophthalmological instrument of FIG. 1 is generally same to that of the conventional alignment optical system for use in an ophthalmological instrument of FIG. 10, identical component parts are denoted by identical reference numerals and duplicate description is avoided. Different components thereof will be described hereinafter.

Figure 2:
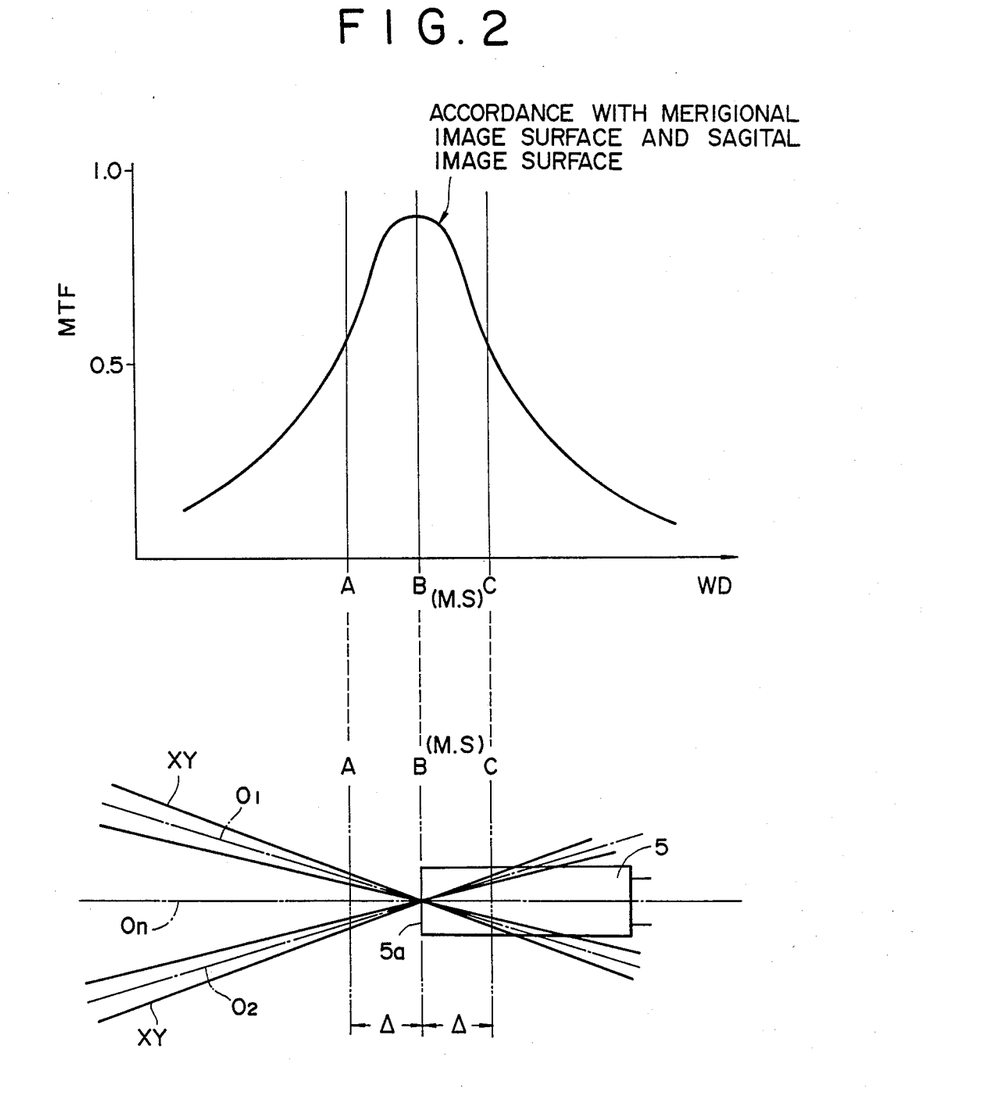
FIG. 2 is an illustration showing the relation between an MTF graph of the working distance alignment optical system of FIG. 1 and an optical path for a ray reaching a photosensitive surface.

In the alignment optical system for use in an ophthalmological instrument according to the first embodiment, a mirror 301 has an optical element of a first target image observing optical system 100 and a mirror 302 as an optical element of a second target image observing optical system 200 have toric surfaces 301a and 302a. The toric surfaces 301a and 302a function as an optical working surface for reflecting a reflecting ray by the cornea towards a photosensitive surface 5a. In this embodiment, the toric surfaces 301a and 302a each have one infinite radius of curvature. That is, the other radius of curvature of each toric surface is designed as such that the meridional image surfaces M of the first and second optical systems 1 and 2 are in alignment with the sagittal image surfaces S thereof, and that both the image surfaces M and S are in alignment with the photosensitive surface 5a of the image pickup tube 5 (see FIG. 2).

Figure 3:
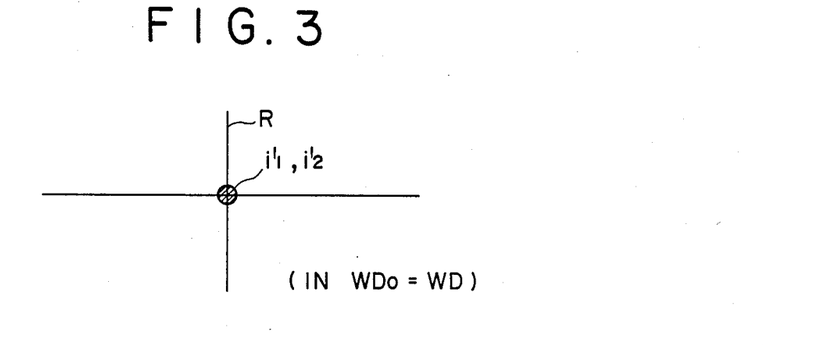
FIG. 3 is an illustration showing an imaged state of a target image when the apparatus main body of the ophthalmological instrument is in the normal working distance.
Figure 4:
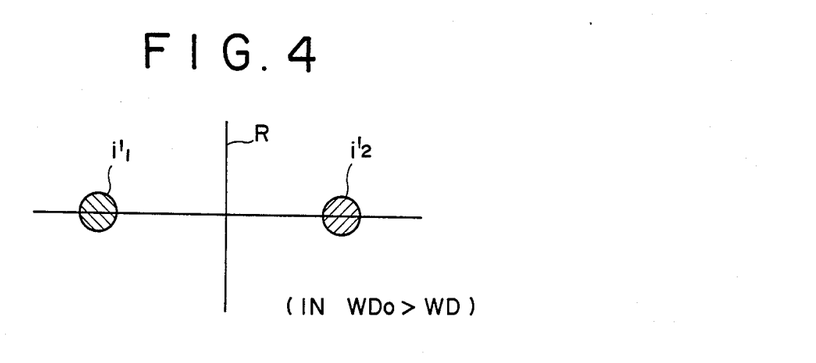
FIG. 4 is an illustration showing an imaged state of a target image when the working distance of the apparatus main body is smaller than the normal working distance.
Figure 5:
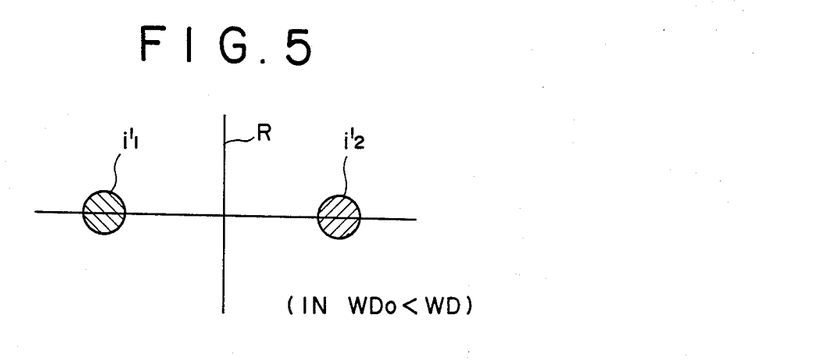
FIG. 5 is an illustration showing an imaged state of a target image when the working distance of the apparatus main body is larger than the normal working distance.

According to the first embodiment, a target image $i_1'$ of the first optical system 1 and a target image $i_2'$ of the second optical system 2, when in a normal working distance $WD_o$, are clearly formed on the photosensitive surface 5a of the image pickup tube 5 by a predetermined power as illustrated in FIG. 3. And, the target images $i_1'$ and $i_2'$ become diffused circular images only when the working distance WD is smaller (see FIG. 4) and larger (see FIG. 5) than the normal working distance $WD_o$. Therefore, since clear and smallest target images $i_1'$ and $i_2'$ can be used during the alignment of the working distance, and the vertical or horizontal alignment, a further improvement of the alignment accuracy of an ophthalmological instrument can be expected.

Second Embodiment

Figure 6:
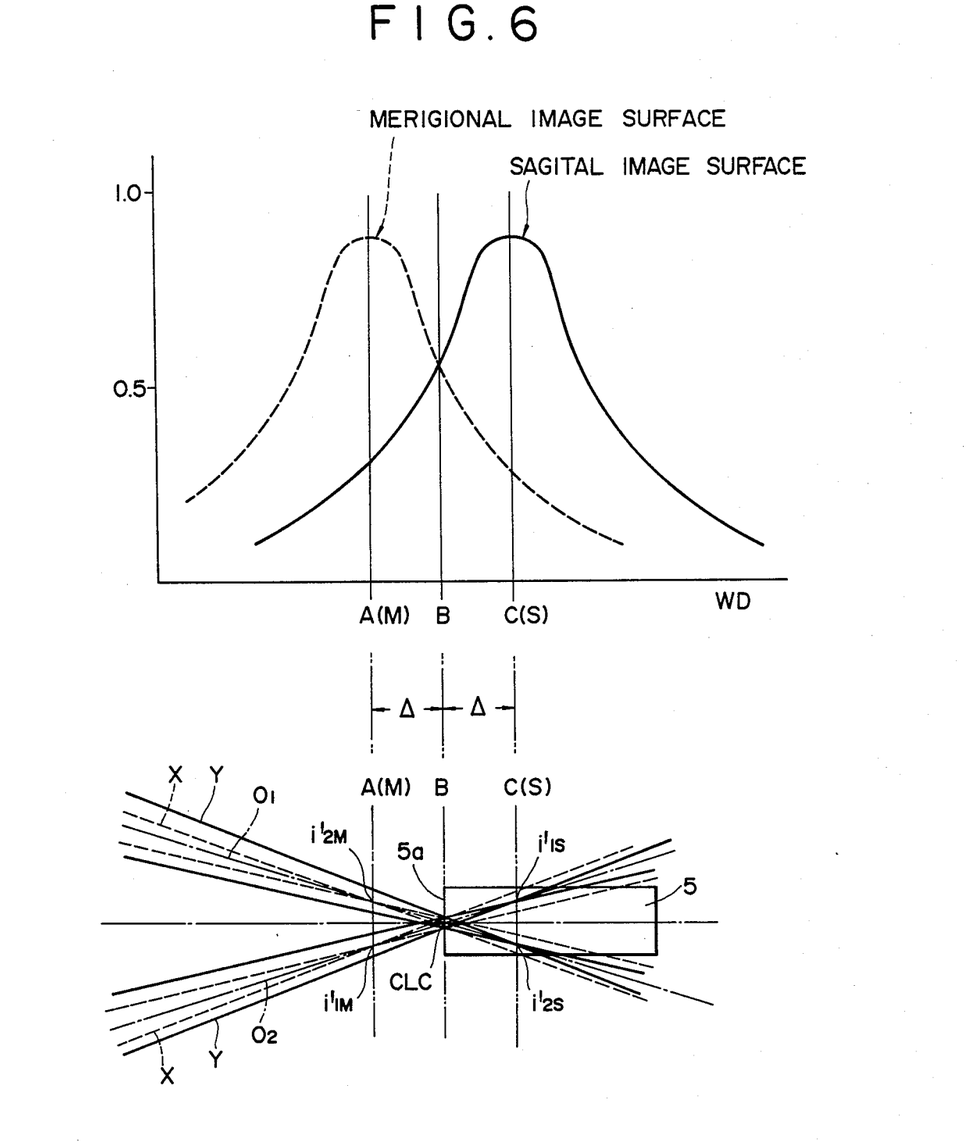
FIG. 6 is an illustration showing a second embodiment of a working distance alignment optical system for use in an ophthalmological instrument according to the present invention and showing a relation between an MTF graph of the working distance alignment optical system and an optical path for a ray reaching a photosensitive surface.

In the second embodiment, one radius of the curvature of torically shaped mirrors 301 and 302 of FIG. 1 is infinite and the other radius of curvature is established as such that the meridional image surface M and the sagittal image surface S can be displaced by a desired amount $\pm\Delta(|\Delta|<|D|)$ with respect to the target image forming position B of the normal working distance $WD_o$(see MTF graph of FIG. 6).

Figure 7:
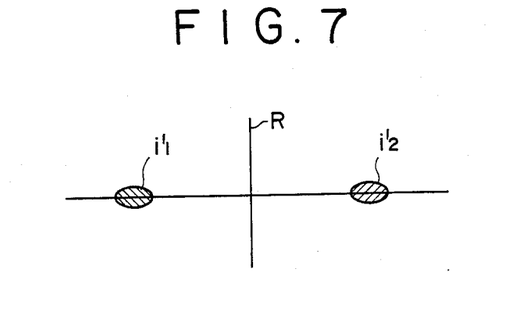
FIGS. 7 through 9 illustrate imaging states of a target image obtained by the second embodiment.
Figure 8:
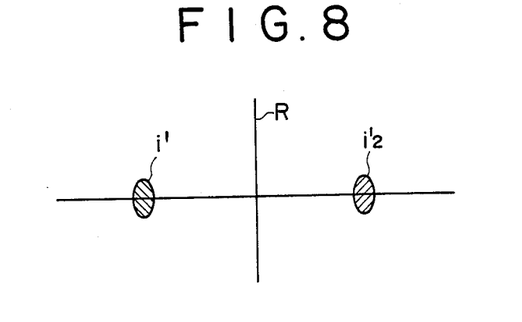
Figure 9:
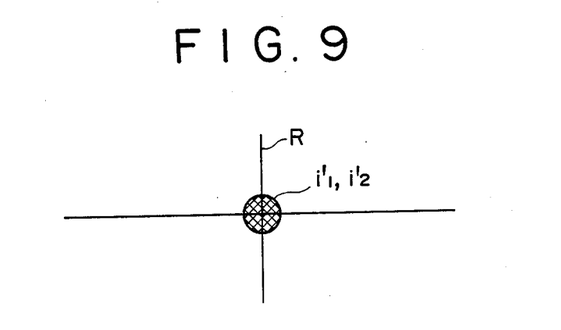

In the second embodiment, when the working distance has been verified so as to bring the photosensitive image 5a in the meridional image surface A(M), the target images $i_1'$ and $I_2$ are clearly formed as, for example, an ellipse having a longitudinal axis in the lateral direction as illustrated in FIG. 7. When the working distance WD has been verified as such that the photosensitive surface 5a is brought to the sagittal image surface C (S), the target images $i_1'$ and $i_2'$ are clearly formed as, for example, an ellipse having a longitudinal axis in the vertical direction as illustrated in FIG. 8. And, when the apparatus main body has been brought to the normal working distance $WD_o$, a circle of least confusion CLC is formed on the photosensitive surface 5a. If the width of a space $2\Delta$ between the meridional image surface A (M) and the sagittal image surface C (S) is properly selected, the size of the circle of least confusion CLC is changed corresponding thereto. By this, a circle of least confusion having a desired size can be obtained.

According to the second embodiment, since the target images $i_1'$ and $i_2'$ are clearly formed with reference to the working distance alignment position and having a different longitudinal axis in front and behind thereof within an ordinary working distance verification range, the user of the ophthalmological instrument can see the target images $i_1'$ and $i_2'$ by eye, and depending on the direction of the longitudinal axes of the target images $i_1'$ and $i_2'$, he can easily judge whether the apparatus main body should be approached towards or brought away from the objective eye E in order to set the apparatus main body to the normal working distance $WD_o$ by one glance.

In the above-described first and second embodiments, the reflecting surfaces as an optical working surface of the mirrors 301 and 302 illustrated in FIG. 1 are toric having one infinite radius of curvature. However, the present invention is not limited to this. For example, at least one refractive surface of the relaying lenses 102 and 202 may be a toric surface in order to obtain the technical effect of the present invention. Similarly, astigmatism correcting lens systems 401 and 402 having at least one toric surface may be provided within optical paths of the first and second target image observing optical system 100 and 200 to attain the technical effect of the present invention.

What is claimed is:

1. A working distance alignment optical system for use in an ophthalmological instrument, comprising:
   target projecting optical means for projecting a target image to a cornea of an eye to be tested, said target projecting means including a target projecting optical axis; and
   target image observing optical means for observing an image of the target in the cornea from a diagonal direction with respect to said target projecting optical axis, at least one of said target projecting optical means and said target image observing optical means being provided with an optical element having a toric surface, said toric surface being configured such that an astigmatism of said target image observing optical means is maintained to determine whether said instrument should be approached to or retreated from the vicinity of the eye to achieve a predetermined working distance between the instrument and the eye.

2. A working distance alignment optical system for use in an ophthalmological instrument, comprising:
   a target projecting optical means for projecting a target image to a cornea of an eye to be tested, said target projecting means including a target projecting optical axis; and
   target image observing optical means for observing an image of the target in the cornea from a diagonal direction with respect to said target projecting optical axis, at least one of said target projecting optical means and said target image observing optical means being provided with an optical element having a cylindrical surface, said cylindrical surface being configured such that an astigmatism of said target image observing optical system is maintained to determine whether said instrument should be approached to or retreated from the vicinity of the eye to achieve a predetermined working distance between the instrument and the eye.

3. A working distance alignment optical system for use in an ophthalmological instrument according to claim 1 or claim 2, wherein said optical element is a mirror.

4. A working distance alignment optical system for use in an ophthalmological instrument, comprising:
   first and second optical systems symmetrically disposed with respect to a median axis therebetween;
   said first optical system having first target image projecting optical means and first target image observing optical means for projecting and observing a first target image onto and from the cornea of an eye, said second optical system having a second target image projecting optical means and a second target image observing optical means for projecting and observing a second target image onto and from the cornea;
   respective optical axes of said first and second target image projecting optical means being partly coincident with the respective optical axes of said first and second projecting optical means, and being diagonally intersected at one point on said median axis;
   said first and second target image observing optical means having a half mirror and a projecting lens disposed in the respective optical paths thereof, rays of light of said first and second target image projecting optical means being reflected by said respective half mirrors toward said respective projecting lenses and converted into parallel pencils of rays by said respective projecting lenses, said respective projecting lenses projecting said parallel pencils of rays to the cornea of the objective eye as target rays of light, said respective target rays of light becoming reflecting rays of light for forming first and second virtual images of said targets by specular reflection from the cornea, respective reflecting rays of light for forming said first and second virtual images being passed through said projecting lens and the half mirror of the other target image observing optical system and proceeding toward respective imaging lenses of said first and second target image observing optical means to verify the alignment of the working distance between the ophthalmological instrument and the eye in accordance with said first and second target images as projected through said respective imaging lenses;
   at least one of the optical elements of said target projecting optical means and said target image observing optical means having a toric surface, said toric surface being configured such that an astigmatism of said target image observing optical means is maintained to determine whether said instrument should be approached to or retreated from the vicinity of the eye to achieve a predetermined working distance between the eye and the instrument.

5. A working distance alignment optical system for use in an ophthalmological instrument, comprising:
   first and second optical systems symmetrically disposed with respect to a median axis therebetween;
   said first optical system having first target image projecting optical means and first target image observing optical means for projecting and observing a first target image onto and from the cornea of an eye, said second optical system having a second target image projecting optical means and a second target image observing optical means for projecting and observing a second target image onto and from the cornea;
   respective optical axes of said first and second target image projecting optical means being partly coincident with the respective optical axes of said first and second projecting optical means, and being diagonally intersected at one point on said median axis;
   said first and second target image observing optical means having a half mirror and a projecting lens disposed in respective optical paths thereof, rays of light of said first and second target image projecting optical means being reflected by said respective half mirrors toward said respective projecting lenses and converted into parallel pencils of rays by said respective projecting lenses, said respective projecting lenses projecting said parallel pencils of rays to the cornea of the objective eye as target rays of light, said respective target rays of light becoming reflecting rays of light for forming first and second virtual images of said targets by specular reflection from the cornea, respective reflecting rays of light for forming said first and second virtual images passing through said projecting lens and said half mirror of the other target image observing optical system and proceeding toward respective imaging lenses of said first and second target image observing optical means to verify the alignment of the working distance between the ophthalmological instrument and the eye in accordance with said first and second target images as projected through said respective imaging lenses;
   at least one of the optical elements of said target projecting optical means and said target image observing optical means having a cylindrical surface, said cylindrical surface being configured such that an astigmatism of said target image observing optical means is maintained to determine whether said instrument should be approached to or retreated from the vicinity of the eye to achieve a predetermined working distance between the eye and the instrument.

6. A working distance alignment optical system for use in an ophthalmological instrument according to claim 4 or claim 5, wherein said optical element is a mirror.

7. A working distance alignment optical system for use in an ophthalmological instrument according to claim 4 or claim 5, wherein said first and second target images are formed on a photosensitive surface of an image pickup tube, and said predetermined working distance is aligned by observing the respective target images formed on said photosensitive surface.

8. A working distance alignment optical system for use in an ophthalmological instrument according to claim 4 or claim 5, wherein said ophthalmological instrument is a noncontact type tonometer, and said median axis is an axis of an air pulse discharging nozzle.

9. A working distance alignment optical system for use in an ophthalmological instrument according to claim 7, wherein when the photosensitive surface of said image pickup tube is positioned in a meridional image surface and in a sagittal image surface which are obtained from a relation between said first and second optical systems and the eye to be tested, an elliptical target image is clearly imaged on said photosensitive surface.

10. A working distance alignment optical system for use in an ophthalmological instrument, comprising:
first and second optical systems symmetrically disposed with respect to a median axis therebetween;
said first optical system having first target image projecting optical means and first target image observing optical means for projecting and observing a first target image onto and from the cornea of an eye, said second optical system having a second target image projecting optical means and a second target image observing optical means for projecting and observing a second target image onto and from the cornea;
respective optical axes of said first and second target image projecting optical means being partly coincident with the respective optical axes of said first and second projecting optical means, and being diagonally intersected at one point on said median axis;
said first and second image observing optical means having a half mirror and a projecting lens disposed in respective optical paths thereof, rays of light of said first and second target image projecting optical means being reflected by said respective half mirrors toward said respective projecting lenses and converted into parallel pencils of rays by said respective projecting lenses, respective projecting lenses projecting said parallel pencils of rays to the cornea of the objective eye as target rays of light, said respective target rays of light becoming reflecting rays of light for forming first and second virtual images of said targets by specular reflection from the cornea, respective reflecting rays of light for forming said first and second virtual images passing through said projecting lens and the half mirror of the other target image observing optical means and proceeding toward respective imaging lenses of said first and second target image observing optical means to verify the alignment of the working distance between the ophthalmological instrument and the eye in accordance with said first and second target images as projected through said respective imaging lenses;
at least one of said optical elements of said target projecting optical means and said target image observing means having a toric surface, said toric surface being configured such that the position of the meridional image surface and the position of the sagittal image surface of said first and second optical systems are displaced with respect to a predetermined working distance aligning position between the instrument and the eye to determine whether said instrument should be approached to or retreated from the vicinity of the eye to achieve said predetermined working distance.

11. A working distance alignment optical system for use in an ophthalmological instrument, comprising:
first and second optical systems symmetrically disposed with respect to a median axis therebetween;
said first optical system having first target image projecting optical means and first target image observing optical means for projecting and observing a first target image onto and from the cornea of an eye, said second optical system having a second target image projecting optical means and a second target image observing optical means for projecting and observing a second target image onto and from the cornea;
respective optical axes of said first and second target image projecting optical means being partly coincident with the respective optical axes of said first and second projecting optical means, and being diagonally intersected at one point on said median;
said first and second image observing optical means having a half mirror and a projecting lens disposed in respective optical paths thereof, rays of light of said first and second target image projecting optical means being reflected by said respective half mirrors toward said respective projecting lenses and converted into parallel pencils of rays by said respective projecting lenses, respective projecting lenses projecting said parallel pencils of rays to the cornea of the objective eye as target rays of light, said respective target rays of light becoming reflecting rays of light for forming first and second virtual images of said targets by specular reflection from the cornea, respective reflecting rays of light for forming said first and second virtual images passing through said projecting lens and the half mirror of the other target image observing optical means and proceeding toward respective imaging lenses of said first and second target image observing optical means to verify the alignment of the working distance between the ophthalmological instrument and the eye in accordance with said first and second target images as projected through said respective imaging lenses;
at least one of said optical elements of said target projecting optical means and said target image observing means having a cylindrical surface, said cylindrical surface being configured such that the position of the meridional image surface and the position of the sagittal image surface of said first and second optical systems are displaced with respect to a predetermined working distance aligning position between the instrument and the eye to determine whether said instrument should be approached to or retreated from the vicinity of the eye to achieve said predetermined working distance.

* * * * *